(12) United States Patent
Ditrich et al.

(10) Patent No.: US 9,115,052 B2
(45) Date of Patent: Aug. 25, 2015

(54) SEPARATION OF AN ENANTIOMER MIXTURE OF (R)- AND (S)-3-AMINO-1-BUTANOL

(75) Inventors: Klaus Ditrich, Goennheim (DE); Michael Bartsch, Hirzel (CH); Harald Winsel, Freinsheim (DE)

(73) Assignee: BASF SE (DE)

( * ) Notice: Subject to any disclaimer, the term of this patent is extended or adjusted under 35 U.S.C. 154(b) by 973 days.

(21) Appl. No.: 13/144,726

(22) PCT Filed: Jan. 15, 2010

(86) PCT No.: PCT/EP2010/050434
§ 371 (c)(1),
(2), (4) Date: Jul. 15, 2011

(87) PCT Pub. No.: WO2010/081865
PCT Pub. Date: Jul. 22, 2010

(65) Prior Publication Data
US 2011/0275855 A1   Nov. 10, 2011

(30) Foreign Application Priority Data
Jan. 16, 2009 (EP) .................................. 09150780

(51) Int. Cl.
| | |
|---|---|
| *C07C 59/00* | (2006.01) |
| *C07C 213/10* | (2006.01) |
| *C07C 51/41* | (2006.01) |
| *C07C 59/50* | (2006.01) |
| *C07C 215/08* | (2006.01) |
| *C07C 217/10* | (2006.01) |

(52) U.S. Cl.
CPC ............ *C07C 213/10* (2013.01); *C07C 51/412* (2013.01); *C07C 59/50* (2013.01); *C07C 215/08* (2013.01); *C07C 217/10* (2013.01); *C07B 2200/07* (2013.01)

(58) Field of Classification Search
CPC ....................................................... C07C 209/88
USPC ........................................................... 562/465
See application file for complete search history.

(56) References Cited

U.S. PATENT DOCUMENTS

| | | |
|---|---|---|
| 6,214,608 B1 | 4/2001 | Balkenhohl et al. |
| 6,713,652 B1 | 3/2004 | Ditrich et al. |
| 7,358,396 B2 * | 4/2008 | Ditrich et al. ................. 564/192 |
| 2006/0122429 A1 | 6/2006 | Ditrich et al. |
| 2008/0021048 A1 | 1/2008 | Bennett et al. |

FOREIGN PATENT DOCUMENTS

| | | |
|---|---|---|
| CN | 1346342 | 4/2002 |
| CS | 208913 | 12/1971 |
| DE | 19956786 A1 | 5/2001 |
| EP | 0801683 A1 | 10/1997 |
| WO | WO 9531436 A1 * | 11/1995 |
| WO | WO-01/38292 A2 | 5/2001 |

OTHER PUBLICATIONS

Besse, P., et al., "Stereoselective chemoenzymatic synthesis of both enantiomers of protected 4-amino-2-pentanone," *Tetrahedron: Asymmetry*, vol. 10, No. 11, pp. 2213-2224 (1999).

* cited by examiner

*Primary Examiner* — Porfirio Nazario Gonzalez
*Assistant Examiner* — Kofi Adzamli
(74) *Attorney, Agent, or Firm* — Drinker Biddle & Reath LLP

(57) ABSTRACT

The present invention relates to a process for separating an enantiomer mixture of (R)- and (S)-3-amino-1-butanol optionally protected on the oxygen atom, and to a process for preparing essentially enantiomerically pure (R)-3-amino-1-butanol which optionally bears a protecting group on the oxygen atom.

15 Claims, No Drawings

SEPARATION OF AN ENANTIOMER MIXTURE OF (R)- AND (S)-3-AMINO-1-BUTANOL

RELATED APPLICATIONS

This application is a national stage application (under 35 U.S.C. §371) of PCT/EP2010/050434, filed Jan. 15, 2010, which claims the benefit of European Application No. 09150780.6, filed Jan. 16, 2009.

The present invention relates to a process for separating an enantiomer mixture of (R)- and (S)-3-amino-1-butanol optionally protected on the oxygen atom, and to a process for preparing essentially enantiomerically pure (R)-3-amino-1-butanol which optionally bears a protecting group on the oxygen atom.

Optically active compounds are of immense significance in the field of the pharmaceutical industry in particular, since frequently only one particular optically active isomer is therapeutically active. There is thus a constantly growth in demand for optically active compounds as reactants for the enantioselective synthesis of active ingredients. One of these key units for the synthesis of a drug for treatment of AIDS symptoms is optically active 3-amino-1-butanol, and especially the (R)-enantiomer thereof.

Attempts by the applicant to split racemic 3-amino-1-butanol benzyl-protected on the oxygen atom into its enantiomers via the route of enzyme-catalyzed selective N-acylation and subsequent hydrolysis did lead to the desired (R)-enantiomer in satisfactory enantiomeric purity, but only via complex and numerous process steps and with an unsatisfactory overall yield.

It was therefore an object of the present invention to provide a more efficient process for preparing essentially enantiomerically pure (S)- and especially (R)-3-amino-1-butanol, which is performable in a few simple steps and with satisfactory yield. More particularly, the process should allow the preparation of (R)-3-amino-1-butanol in an enantiomeric purity of at least 98% ee, preferably at least 99% ee, more preferably at least 99.5% ee, even more preferably at least 99.6% ee and especially at least 99.8% ee.

It has been found that, surprisingly, the use of essentially enantiomerically pure mandelic acid, i.e. of (S)- or (R)-mandelic acid, allows the preparation of (R)-3-amino-1-butanol and if desired also of (S)-3-amino-1-butanol, and also of the corresponding compounds protected on the oxygen atom, in high enantiomeric purities and also satisfactory yields.

The invention therefore provides a process for separating an enantiomer mixture of (R)- and (S)-3-amino-1-butanol optionally protected on the oxygen atom, comprising the following steps:
(i) reacting an enantiomer mixture of the compounds of the formulae I-R and I-S

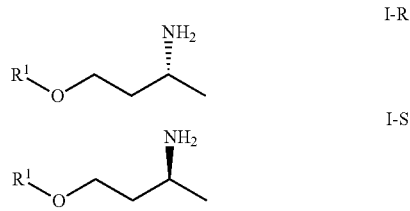

in which $R^1$ is hydrogen or a protecting group
with (S)- or (R)-mandelic acid and an acid different from this (S)- or (R)-mandelic acid used;
(ii) removing and isolating the (S)- or (R)-mandelic salt of the compound of the formula I-R formed in step (i);
(iii) optionally purifying the (S)- or (R)-mandelic salt of the compound of the formula I-R isolated in step (ii);
(iv) releasing the compound of the formula I-R from the (S)- or (R)-mandelic salt thereof and if desired deprotecting the compound of the formula I-R in which $R^1$ is not hydrogen to obtain (R)-3-amino-1-butanol; and
(v) if desired releasing the (enriched) compound of the formula I-S and if desired deprotecting the compound of the formula I-S in which $R^1$ is not hydrogen to obtain (enriched) (S)-3-amino-1-butanol.

The invention also provides a process for preparing essentially enantiomerically pure (R)-3-amino-1-butanol which optionally bears a protecting group on the oxygen atom, comprising the following steps:
(i) reacting an enantiomer mixture of the compounds of the formulae I-R and I-S

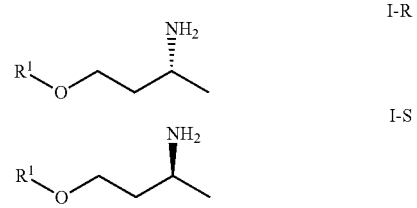

in which $R^1$ is hydrogen or a protecting group
with (S)- or (R)-mandelic acid and an acid different from this (S)- or (R)-mandelic acid used;
(ii) removing and isolating the (S)- or (R)-mandelic salt of the compound of the formula I-R formed in step (i);
(iii) optionally purifying the (S)- or (R)-mandelic salt of the compound of the formula I-R isolated in step (ii); and
(iv) releasing the compound of the formula I-R from the (S)- or (R)-mandelic salt thereof and if desired deprotecting the compound of the formula I-R in which $R^1$ is not hydrogen to obtain (R)-3-amino-1-butanol.

The expression "(R)- and (S)-3-amino-1-butanol which bear a protecting group on the oxygen atom" refers, respectively, to the compounds I-R and I-S in which $R^1$ is not H.

In the context of the present invention, $C_1$-$C_3$-alkyl represents an alkyl radical having 1 to 3 carbon atoms, i.e. methyl, ethyl, propyl or isopropyl.

$C_1$-$C_4$-Alkyl represents an alkyl radical having 1 to 4 carbon atoms, i.e. methyl, ethyl, propyl, isopropyl, n-butyl, sec-butyl, isobutyl or tert-butyl.

$C_1$-$C_3$-Alkoxy represents a $C_1$-$C_3$-alkyl radical which is bonded via an oxygen atom. Examples thereof are methoxy, ethoxy, propoxy and isopropoxy.

$C_1$-$C_3$-Alkoxy-$C_1$-$C_3$-alkyl represents a $C_1$-$C_3$-alkyl radical in which one hydrogen atom is replaced by a $C_1$-$C_3$-alkoxy group. Examples thereof are methoxymethyl, 1- and 2-methoxyethyl, 1-, 2- and 3-methoxypropyl, 1- and 2-methoxyprop-2-yl, ethoxymethyl, 1- and 2-ethoxyethyl, 1-, 2- and 3-ethoxypropyl, 1- and 2-ethoxyprop-2-yl, propoxymethyl, 1- and 2-propoxyethyl, 1-, 2- and 3-propoxypropyl, 1- and 2-propoxyprop-2-yl and the like.

The remarks made hereinafter regarding preferred configurations of the processes according to the invention, and of the reactants, reaction conditions and products, apply either taken alone or, more particularly, in combination with one another.

The remarks apply to both processes according to the invention where they overlap.

In the context of the present invention, essentially enantiomerically pure compounds, especially essentially enantiomerically pure (R)-3-amino-1-butanol shall be understood to mean that they are present in an enantiomeric purity of at least 95% ee, preferably at least 96% ee, more preferably at least 98% ee, even more preferably at least 99% ee, even more especially preferably at least 99.5% ee, particularly at least 99.6% ee and especially at least 99.8% ee.

"(R)-Mandelic acid" means essentially enantiomerically pure (R)-mandelic acid, i.e. (R)-mandelic acid in an enantiomeric purity of at least 95% ee, preferably at least 96% ee, more preferably at least 98% ee, even more preferably at least 99% ee, even more especially preferably at least 99.5% ee and especially at least 99.6% ee.

Correspondingly, "(S)-mandelic acid" means essentially enantiomerically pure (S)-mandelic acid, i.e. (S)-mandelic acid in an enantiomeric purity of at least 95% ee, preferably at least 96% ee, more preferably at least 98% ee, even more preferably at least 99% ee, even more especially preferably at least 99.5% ee and especially at least 99.6% ee.

The unit "% ee" relates to the enantiomeric excess and is thus a measure of the enantiomeric purity, which is also referred to as optical purity. This is calculated from the difference between the molar proportions of the two enantiomers in an enantiomeric mixture. For example, 95% ee means that the proportion of the main enantiomer in the enantiomer mixture is 97.5% and the proportion of the mirror-image compound thereof is 2.5%.

The compounds I-R and I-S are, respectively, (R)- and (S)-3-amino-1-butanol optionally protected on the oxygen atom ("O-protected").

In the enantiomer mixture used in step (i), $R^1$ in the compounds I-R and I-S has the same definition in each case.

In step (i), the enantiomer mixture used may be the racemate of the compounds I-R and I-S; mixtures in which one of the enantiomers is enriched are equally suitable though. Since, however, the customary synthesis of optionally O-protected 3-amino-1-butanol leads to the racemate thereof, the racemate of the compounds I-R and I-S is frequently used in step (i).

Suitable protecting groups (i.e. suitable definitions of $R^1$ where it is not hydrogen) are, for example, $C_1$-$C_4$-alkyl, allyl, propargyl, $C_1$-$C_3$-alkoxy-$C_1$-$C_3$-alkyl and optionally substituted benzyl, such as benzyl, methylbenzyl, e.g. 2-, 3- or 4-methylbenzyl, or methoxybenzyl, e.g. 2-, 3- or 4-methoxybenzyl. Among these, preference is given to $C_1$-$C_4$-alkyl (i.e. methyl, ethyl, propyl, isopropyl, n-butyl, sec-butyl, isobutyl or tent-butyl) and optionally substituted benzyl, such as benzyl, methylbenzyl, e.g. 2-, 3- or 4-methylbenzyl, or methoxybenzyl, e.g. 2-, 3- or 4-methoxybenzyl.

$R^1$ is therefore preferably hydrogen, $C_1$-$C_4$-alkyl or optionally substituted benzyl, such as benzyl, methylbenzyl, e.g. 2-, 3- or 4-methylbenzyl, or methoxybenzyl, e.g. 2-, 3- or 4-methoxybenzyl, more preferably hydrogen, $C_1$-$C_4$-alkyl or benzyl and even more preferably hydrogen, tert-butyl or benzyl. More particularly, $R^1$, however, is hydrogen; i.e., in step (i) of the process according to the invention, especially an enantiomer mixture of (R)- and (S)-3-amino-1-butanol is used.

In step (i), (S)- or (R)-mandelic acid is used. The mandelic acid enantiomer is preferably selected such that it forms, with the compound I-R, the salt with the lowest solubility product of the salts theoretically possible in step (i) (especially with a lower solubility product than the salt of the compound I-R with the opposite mandelic acid antipode and of course also than the salt of the compound I-S with the selected mandelic acid antipode) in the reaction medium used. In the case of selection of the preferred solvents specified below, preference is given to using (S)-mandelic acid when $R^1$ in the compounds I-R and I-S is hydrogen or optionally substituted benzyl. When $R^1$, in contrast, is $C_1$-$C_4$-alkyl and especially tert-butyl, it is preferred to use (R)-mandelic acid in step (i).

The (S)- or (R)-mandelic acid used in step (i) is preferably used in an amount of 0.8 to 1.5 mol, more preferably of 0.8 to 1.2 mol, even more preferably of 0.9 to 1.1 mol and even more especially preferably of 1 to 1.1 mol, e.g. 1 to 1.05 mol, based on 1 mol of the compound I-R which is present in the enantiomer mixture used in step (i). More particularly, (S)- or (R)-mandelic acid is used in an approximately equimolar amount, based on the amount of compound I-R present in the enantiomer mixture. "Approximately equimolar" is intended to express that error tolerances, which result, for example, from measurement imprecisions of the balances and/or from the purity of the reactants, are also covered by the term "equimolarity".

When the enantiomer mixture used in step (i) is the racemate of the compounds I-R and I-S, (S)- or (R)-mandelic acid is used in an amount of preferably 0.4 to 0.75 mol, more preferably of 0.4 to 0.6 mol, even more preferably of 0.45 to 0.55 mol and even more especially preferably of 0.5 to 0.55 mol, e.g. 0.5 to 0.525 mol, based on 1 mol of the racemate. More particularly, (S)- or (R)-mandelic acid is used in an amount of approximately 0.5 mol, based on 1 mol of the racemate. With regard to the term "approximately", reference is made mutatis mutandis to the statements made above with regard to "approximately equimolar".

The acid different from (S)- or (R)-mandelic acid used in step (i) is preferably used in an amount of 0.8 to 1.5 mol, more preferably of 0.8 to 1.2 mol, even more preferably of 0.9 to 1.1 mol and even more especially preferably of 1 to 1.1 mol, e.g. 1 to 1.05 mol, based on 1 mol of the compound I-S which is present in the enantiomer mixture used in step (i). More particularly, this acid is used in an approximately equimolar amount, based on the amount of compound I-S present in the enantiomer mixture. With regard to the term "approximately equimolar", reference is made to the above remarks. The above statements regarding the amount of acid are based on monoprotic acids; in the case of di- or triprotic acids whose acid strength is sufficiently great that the second and third protons can protonate the amino group of the reactant, the amounts reduced by a factor of 2 or 3 apply correspondingly.

When the enantiomer mixture used in step (i) is the racemate of the compounds I-R and I-S, the acid different from (S)- or (R)-mandelic acid is used in an amount of 0.4 to 0.75 mol, more preferably of 0.4 to 0.6 mol, even more preferably of 0.45 to 0.55 mol and even more especially preferably of 0.5 to 0.55 mol, e.g. 0.5 to 0.525 mol, based on 1 mol of the racemate. More particularly, this acid is used in an amount of approximately 0.5 mol, based on 1 mol of the racemate. With regard to the term "approximately", reference is made mutatis mutandis to the statements made above regarding "approximately equimolar". Equally, reference is made to the statements made above for the case of di- or triprotic acids.

The selection of the acid different from (S)- or (R)-mandelic acid is not subject to any specific requirements; it should, however, not adversely affect salt formation between the compound I-R and the (S)- or (R)-mandelic acid used; this acid should especially not, with the compound I-R, form an acid addition salt with a lower solubility product in the reaction medium of step (i) than the salt of the (S)- or (R)-mandelic acid used with the compound I-R. The acid should also not act oxidatively. Moreover, it should be at least partly soluble in the reaction medium of step (i) and should of course possess a sufficiently high $pK_a$ to be able to protonate the compound I-S under the reaction conditions of step (i). In addition, it should form, with the compound I-S, a salt with very good solubility under the reaction conditions of step (i). The acid need not be chiral; achiral acids are entirely sufficient at least for the process according to the invention, which serves to prepare essentially enantiomerically pure (R)-3-amino-1-butanol, and are preferred for reasons of cost and availability. Chiral acids are, however, entirely suitable; for example, it is possible to use the opposite enantiomer of the (S)- or (R)-mandelic acid used in step (i). When the racemate of the compounds I-R and I-S is used in step (i), it is possible, for example, to use racemic mandelic acid overall in step (i). The use of chiral acids is a possibility, for example, when essentially enantiomerically pure I-S is also to be obtained.

The acid used is preferably a monoprotic acid.

Suitable achiral acids are, for example, inorganic acids such as hydrogen chloride (gaseous), hydrochloric acid, hydrobromic acid or sulfuric acid, or organic acids, for example aliphatic monocarboxylic acids having preferably 1 to 6 carbon atoms, such as formic acid, acetic acid, trifluoroacetic acid, propionic acid, butyric acid, valeric acid, isovaleric acid and caproic acid, aromatic carboxylic acids such as benzoic acid, and sulfonic acids such as methanesulfonic acid, trifluoromethanesulfonic acid or toluenesulfonic acid. Also suitable are mixtures of the aforementioned acids. Among these, preference is given to aliphatic monocarboxylic acids having 1 to 3 carbon atoms, such as formic acid, acetic acid, trifluoroacetic acid and propionic acid, and mixtures thereof. More particularly, acetic acid is used.

Step (i) is preferably performed in a suitable solvent. Suitable solvents are preferably those in which the reactants are soluble but—at least within a particular temperature range—the salt of the (S)- or (R)-mandelic acid used with the compound I-R is insoluble or does not have good solubility, the acid addition salt of the compound I-S still being sufficiently soluble within the same temperature range. Particularly suitable solvents have been found to be $C_1$-$C_4$-alcohols such as methanol, ethanol, propanol, isopropanol, n-butanol, sec-butanol, isobutanol and tert-butanol, and mixtures thereof, which optionally comprise water in an amount of 0.05 to 10% by weight, preferably 0.1 to 10% by weight, more preferably 0.1 to 5% by weight, even more preferably 0.1 to 1% by weight and especially 0.1 to 0.5% by weight, based on the total weight of the $C_1$-$C_4$-alcohols and water.

In the case that $R^1$ is H, it is preferred that the alcohols comprise 0.05 to 10% by weight, more preferably 0.1 to 10% by weight, even more preferably 0.1 to 5% by weight, even more especially preferably 0.1 to 1% by weight, particularly 0.1 to 0.5% by weight and especially 0.2 to 0.5% by weight of water, based on the total weight of the $C_1$-$C_4$-alcohols and water.

A particularly preferred solvent is isopropanol, which may comprise 0.05 to 10% by weight, preferably 0.1 to 10% by weight of water, more preferably 0.1 to 5% by weight, even more preferably 0.1 to 1% by weight, particularly 0.1 to 0.5% by weight and especially 0.2 to 0.5% by weight of water, based on the total weight of isopropanol and water.

In the case that $R^1$ is H, a particularly preferred solvent is isopropanol, which comprises 0.05 to 10% by weight, preferably 0.1 to 10% by weight of water, more preferably 0.1 to 5% by weight, even more preferably 0.1 to 1% by weight, particularly 0.1 to 0.5% by weight and especially 0.2 to 0.5% by weight of water, based on the total weight of isopropanol and water.

In the case that $R^1$ is not hydrogen, the alcohols may also be essentially anhydrous, i.e. comprise less than 0.05% by weight of water, based on the total weight of alcohol and water.

Step (i) is performed, for example, in such a way that the enantiomer mixture is initially charged in a suitable solvent and admixed with the (S)- or (R)-mandelic acid and the acid different therefrom simultaneously or successively, all at once, in portions or continuously. When the two acids are added successively, the sequence of addition, i.e. whether first the (S)- or (R)-mandelic acid and then the acid different therefrom is added, or vice versa, is irrelevant. Preferably, however, the two acids are not added all at once, but instead continuously or in portions. The enantiomer mixture is preferably initially charged at room temperature; however, it is also possible to heat the initial charge before the addition of the acids, for example to a temperature of >25° C. up to the boiling point of the solvent, which can, however, complicate reaction control when the salt formation is exothermic. Therefore, the enantiomer mixture is preferably initially charged at room temperature.

The admixing of the enantiomer mixture with the (S)- or (R)-mandelic acid and the acid different therefrom forms the acid addition salts of the compounds I-R and I-S. When the abovementioned preferred solvents are selected, the (S)- or (R)-mandelic salt of the compound I-R and optionally also the acid addition salt of the compound I-S are insoluble or at least incompletely soluble at room temperature and therefore precipitate in the course of formation thereof. The desired (S)- or (R)-mandelic salt of the compound I-R therefore has to be removed and isolated from the precipitate.

In the case of selection of the abovementioned preferred solvents, the (S)- or (R)-mandelic salt of the compound I-R is preferably removed and isolated by precipitating it and isolating the precipitate. Since, as stated, the acid addition salts of the compounds I-R and I-S are generally insoluble or incompletely soluble in the above-described preferred solvents at room temperature (i.e. at the preferred temperature of step (i)), they are first brought into solution, which is preferably accomplished by heating, preferably to a temperature of 30° C. up to the boiling point of the mixture, more preferably of 50° C. up to the boiling point of the mixture and especially up to the boiling point of the mixture. Subsequently, the solution is cooled. The cooling must not be too rapid, in order that the different acid addition salts which possess different solubility products precipitate successively and not simultaneously. In the course of cooling, the acid addition salt with the lowest solubility product in the solvent used precipitates out first. This is generally—at least when the abovementioned preferred acids different from the (S)- or (R)-mandelic acid used and the abovementioned preferred solvents are selected—the (S)- or (R)-mandelic salt of the compound I-R; this is then isolated from the mixture. The isolation can be effected by means of known processes, such as filtration, sedimentation or centrifugation. When the acid addition salt of the compound I-S is nevertheless precipitated first, it is isolated substantially completely and then the solution is cooled further until the (S)- or (R)-mandelic acid salt of the compound I-R precipitates, and is then isolated. When the above-described preferred solvents S and the above-described preferred acids are selected, which are of course selected such that the solubility product of the acid addition salt thereof with the compound I-S in the preferred solvents is higher than the solubility product of the (S)- or (R)-mandelic salt of the compound I-R, the (S)- or (R)-mandelic salt of the compound I-R will, however, precipitate first.

In a preferred embodiment, the (S)- or (R)-mandelic salt of the compound I-R which has been isolated in step (ii) is subsequently purified once or more than once, for example once, twice or three times.

The purification is accomplished preferably by single or repeated, for example single, double or triple, recrystallization. Solvents suitable for the recrystallization are the abovementioned $C_1$-$C_4$-alcohols and mixtures thereof, and the mixtures thereof with water, for example with water in an amount of 0.1 to 10% by weight, preferably 0.5 to 5% by weight, more preferably 1 to 5% by weight and especially of 1 to 3% by weight, based on the total weight of alcohol and water. The preferred alcohol for recrystallization too is isopropanol and mixtures thereof with water, for example water in an amount of 0.1 to 10% by weight, preferably 0.5 to 5% by weight, more preferably 1 to 5% by weight and especially of 1 to 3% by weight, based on the total weight of isopropanol and water. When recrystallization is effected more than once, different solvents or solvent mixtures may be used for the different recrystallization steps. For example, it is possible to recrystallize once in a $C_1$-$C_4$-alcohol, preferably in isopropanol, and once in an alcohol-water mixture, preferably an isopropanol-water mixture with 0.1 to 10% by weight, preferably 0.5 to 5% by weight, more preferably 1 to 5% by weight and especially 1 to 3% by weight of water, based on the total weight of isopropanol and water.

The compound I-R is released from the (S)- or (R)-mandelic salt thereof in step (iv) preferably by reacting the (S)- or (R)-mandelic salt of the compound I-R obtained in step (ii) or (iii) with a base in a suitable solvent.

Typically, an aqueous basic solution is used for this purpose, for example aqueous NaOH or aqueous KOH, and the free amine is isolated by distillation or by extraction into an organic solvent, such as diethyl ether or methyl tert-butyl ether. In the case of (R)-3-amino-1-butanol (compound I-R in which $R^1$ is H), this procedure, however, is not very suitable, since the free (R)-3-amino-1-butanol is firstly completely miscible with water, such that an extraction with organic solvents is impossible or only very incomplete, and the boiling point of (R)-3-amino-1-butanol is secondly above that of water, such that it can be removed from the remaining reaction products and impurities only with great complexity, if at all.

Especially in the case of the mandelic salt of (R)-3-amino-1-butanol (this is preferably the (S)-mandelic salt), the solvent is preferably selected such that, on the one hand, the reactants, i.e. the mandelic salt of (R)-3-amino-1-butanol and the base, are at least partly soluble therein, and, on the other hand, the (R)-3-amino-1-butanol released can be removed therefrom easily. "Partly soluble" means that at least 5% by weight, preferably at least 10% by weight, of the salt used and of the base used is soluble in the solvent.

The solvent is preferably selected such that it has a boiling point at least 10° C. higher, preferably at least 20° C. higher, more preferably at least 50° C. higher and especially at least 80° C. higher than 3-amino-1-butanol.

Solvents which satisfy the abovementioned conditions are, for example, organic amines (in the context of the present invention, this term also comprises amino alcohols) with a melting point of preferably at most 50° C. and a boiling point of preferably at least 180° C., more preferably at least 200° C., such as diethanolamine and triethanolamine, diethylene glycol, triethylene glycol and higher polyethylene glycols, nitrobenzene and dimethyl sulfoxide. Preferred solvents are organic amines with a melting point of preferably at most 50° C. and a boiling point of preferably at least 180° C., more preferably at least 200° C., such as diethanolamine and triethanolamine. Especially triethanolamine is used.

Preferred bases are at least partly soluble in the solvents mentioned and possess sufficient basicity to release the (R)-3-amino-1-butanol from the mandelic salt thereof.

Accordingly, preferred bases have a higher $pK_a$ than (R)-3-amino-1-butanol. Moreover, the product formed from the base in the release reaction (for example methanol in the case of use of a methoxide) should be readily removable from the (R)-3-amino-1-butanol released. Examples of preferred bases are alkali metal $C_1$-$C_4$-alkoxides such as sodium methoxide, potassium methoxide, sodium ethoxide, potassium ethoxide, sodium propoxide, potassium propoxide, sodium isopropoxide, potassium isopropoxide, sodium n-butoxide, potassium n-butoxide, sodium tert-butoxide and potassium tert-butoxide. Particularly preferred bases are alkali metal $C_1$-$C_3$-alkoxides such as sodium methoxide, potassium methoxide, sodium ethoxide, potassium ethoxide, sodium propoxide, potassium propoxide, sodium isopropoxide and potassium isopropoxide. More highly preferred bases are alkali metal $C_1$-$C_2$-alkoxides such as sodium methoxide, potassium methoxide, sodium ethoxide and potassium ethoxide. Particularly sodium methoxide or sodium ethoxide and especially sodium methoxide is used.

The base is preferably used in at least equimolar amounts in relation to the mandelic salt of (R)-3-amino-1-butanol, more preferably in an amount of 1 to 2 mol, even more preferably of 1 to 1.5 mol, even more especially preferably of 1 to 1.3 mol and especially of 1 to 1.1 mol, based on 1 mol of the mandelic salt of (R)-3-amino-1-butanol.

The procedure in step (iv) is preferably to initially charge the acid addition salt in the solvent, optionally to heat it and to admix it with the base. Alternatively, the acid addition salt can be initially charged in the solvent, admixed with the base and only then optionally heated. The heating is effected preferably to a temperature of 30 to 100° C., more preferably of 50 to 100° C. and especially of 70 to 90° C. Subsequently, the (R)-3-amino-1-butanol released is removed from the reaction mixture, which is preferably accomplished by (fractional) distillation, preferably under reduced pressure.

This procedure is also suitable for compounds I-R in which $R^1$ is not H; here, however, it is also possible to use water as the solvent and a water-soluble base such as potassium hydroxide or sodium hydroxide. Since compounds I-R in which $R^1$ is not H are essentially immiscible with water, they can be isolated, for example, by extraction into an organic solvent which is in turn essentially immiscible with water, and then removing the organic solvent, for example by distillation, optionally under reduced pressure. Suitable organic solvents are, for example, aliphatic hydrocarbons such as pentane, hexane, heptane and octane, cycloaliphatic hydrocarbons such as cyclohexane and cyclooctane, chloroalkanes such as dichloromethane, chloroform, carbon tetrachloride, di- and trichloroethane, aromatic hydrocarbons such as benzene, toluene and the xylenes, aliphatic ethers such as diethyl ether, dipropyl ether, dibutyl ether, methyl isobutyl ether and methyl tert-butyl ether, and carboxylic esters such as ethyl acetate, propyl acetate, ethyl propionate and propyl propionate. Among these, preference is given to the aliphatic ethers mentioned and especially diethyl ether.

The compound I-R is subsequently, if desired and if required, i.e. in the case that $R^1$ is not hydrogen, deprotected to (R)-3-amino-1-butanol.

For this purpose, it is possible to employ the deprotection reactions customary for the particular protecting group. For instance, a methyl protecting group ($R^1$=$CH_3$) can be removed by reaction with HCl, HBr, HI, Si(CH$_3$)$_3$I or BBr$_3$; higher alkyl radicals (R$^1$=C$_2$-C$_4$-alkyl) can be removed by means of anhydrous trifluoroacetic acid or HBr, and benzylic protecting groups can be detached by hydrogenolytic means.

The resulting (R)-3-amino-1-butanol can finally, if desired, be purified further, which can be accomplished, for example, by distillative or extractive means.

A particularly preferred embodiment of the invention relates to a process for separating an enantiomer mixture of (R)- and (S)-3-amino-1-butanol, comprising the following steps:
(i) reacting an enantiomer mixture of (R)- and (S)-3-amino-1-butanol with (S)-mandelic acid and an acid different from (S)-mandelic acid;
(ii) removing and isolating the (S)-mandelic salt of (R)-3-amino-1-butanol formed in step (i);
(iii) optionally purifying the (S)-mandelic salt of (R)-3-amino-1-butanol isolated in step (ii);
(iv) releasing (R)-3-amino-1-butanol from the (S)-mandelic salt thereof; and
(v) if desired, releasing (S)-3-amino-1-butanol.

A particularly preferred embodiment of the invention also relates to a process for preparing essentially enantiomerically pure (R)-3-amino-1-butanol, comprising the following steps:
(i) reacting an enantiomer mixture of (R)- and (S)-3-amino-1-butanol with (S)-mandelic acid and an acid different from (S)-mandelic acid;
(ii) removing and isolating the (S)-mandelic salt of (R)-3-amino-1-butanol formed in step (i);
(iii) optionally purifying the (S)-mandelic salt of (R)-3-amino-1-butanol isolated in step (ii); and
(iv) releasing (R)-3-amino-1-butanol from the (S)-mandelic salt thereof.

With regard to suitable and preferred acids different from (S)-mandelic acid, the amounts of (S)-mandelic acid used in step (i) and of the acid different therefrom, the solvents and reactants used in the individual steps, for example bases, and further suitable and preferred reaction conditions and process measures, reference is made to the above remarks.

A specific embodiment of the invention relates to a process for preparing (R)-3-amino-1-butanol, comprising the following steps:
(a) reacting an enantiomer mixture of (R)- and (S)-3-amino-1-butanol with (S)-mandelic acid and acetic acid in isopropanol as a solvent, which comprises 0.1 to 1% by weight of water, based on the total weight of isopropanol and water, using (S)-mandelic acid in an amount of 0.1 to 1.1 mol, based on 1 mol of the (R)-3-amino-1-butanol present in the enantiomer mixture, and using acetic acid in an amount of 0.1 to 1.1 mol, based on 1 mol of the (S)-3-amino-1-butanol present in the enantiomer mixture;
(b) heating the mixture obtained in step (a) until the acid addition salts formed and precipitated in step (a) have dissolved;
(c) cooling the solution obtained in step (b) until a precipitate forms;
(d) removing and isolating the precipitate formed in step (c);
(e) recrystallizing the precipitate isolated in step (d) once or more than once in isopropanol and/or isopropanol which comprises 0.1 to 5% by weight of water, based on the total weight of isopropanol and water;
(f) reacting the (S)-mandelic salt of (R)-3-amino-1-butanol obtained in step (e) with an alkali metal C$_1$-C$_4$-alkoxide, preferably with sodium methoxide or sodium ethoxide and especially with sodium methoxide, in an organic amine with a melting point of at most 50° C. and a boiling point of at least 180° C., preferably in diethanolamine or especially in triethanolamine at a temperature of 50 to 100° C.;
(g) distillatively removing the (R)-3-amino-1-butanol released in step (f); and
(h) optionally further purifying the (R)-3-amino-1-butanol obtained in step (g).

The purification in step (h) can be effected, for example, by distillation or extraction, as described above.

If (S)-3-amino-1-butanol is also to be obtained by the process according to the invention, the acid addition salt of the compound I-S is isolated in step (ii). This is accomplished, for example, as already mentioned, by further cooling the solution from which already precipitated (S)- or (R)-mandelic salt of the compound I-R has been isolated until the acid addition salt of the compound I-S also precipitates out. The latter can, as already described for the (S)- or (R)-mandelic salt of the compound I-R, be isolated, for example, by filtration, sedimentation or centrifugation, and then purified further analogously, for example by single or multiple recrystallization. The release of the compound I-S from the acid addition salt thereof and the possible deprotection to give enriched (S)-3-amino-1-butanol can be accomplished analogously to the above-described release and possible deprotection to obtain (R)-3-amino-1-butanol.

In order to obtain (S)-3-amino-1-butanol in a particularly high enantiomeric purity, it is preferred, in step (i), to use, as the acid different from (S)- or (R)-mandelic acid, the antipode of this mandelic acid used.

Racemic 3-amino-1-butanol is commercially available or can be obtained by known literature methods, as described, for example, in Chemical Abstracts 1949, 6199 or in J. Am. Chem. Soc. 1957, 79(14), 3839-3846.

(S)- and (R)-mandelic acid are likewise commercially available.

O-protected 3-amino-1-butanol is obtained by customary methods of protecting group introduction, for example by reaction of N-protected 3-amino-1-butanol with an R$^1$ halide (R$^1$ is not H), such as methyl iodide, tert-butyl chloride or benzyl chloride, and then removing the N-protecting group. One example of a suitable N-protecting group is Boc, which, after attachment of the O-protecting group, can be removed again easily and selectively, for example by acidic hydrolysis.

The benzyl protecting group is preferably introduced by the method described in DE-A-19956786.

However, the use of O-protecting groups is unnecessary for the inventive separation processes, and so preference is given to proceeding from enantiomer mixtures of 3-amino-1-butanol and especially from racemic 3-amino-1-butanol.

The invention further provides the (S)-mandelic salt of the compound I-R, in which R$^1$ is H or optionally substituted benzyl and preferably H or benzyl. This inventive (S)-mandelic salt preferably has an enantiomeric purity of at least 98% ee, more preferably at least 99% ee, even more preferably at least 99.5% ee, even more especially preferably at least 99.6% ee and especially at least 99.8% ee.

The invention further provides the (R)-mandelic acid of the compound I-S, in which R$^1$ is C$_1$-C$_4$-alkyl and especially tert-butyl. This inventive (R)-mandelic salt preferably has an enantiomeric purity of at least 98% ee, more preferably at least 99% ee, even more preferably at least 99.5% ee, even more especially preferably at least 99.6% ee and especially at least 99.8% ee.

The processes according to the invention afford (R)-3-amino-1-butanol with a high enantiomeric purity of preferably at least 98% ee, more preferably at least 99% ee, even more preferably of at least 99.5% ee, even more especially preferably at least 99.6% ee and especially at least 99.8% ee, and a chemical purity of preferably at least 98%, more preferably at least 99% and especially of at least 99.5%, in a satisfactory overall yield in a few simple reaction steps which do not require any complex reactants or any protecting group techniques. If desired, the corresponding S enantiomer is also obtained in a good chemical purity and enantiomeric purity.

The enantiomeric excess can be determined by means of common processes, for example by determination of the optical rotation, or by chromatography on a chiral phase, for example by HPLC or gas chromatography using chiral columns.

The invention will now be illustrated by the nonlimiting examples which follow.

EXAMPLES

1. Enantiomer Separation of Racemic 3-amino-1-butanol
1.1 Preparation of the (S)-mandelic Salt of (R)-3-amino-1-butanol A mixture of racemic 3-amino-1-butanol (638 g, 7.16 mol), isopropanol (4.3 l) and water (8.6 ml) was admixed successively while stirring with (S)-mandelic acid (544 g, 3.58 mol) and acetic acid (214.8 g, 3.58 mol). The reaction mixture was heated to boiling until the precipitated salts had dissolved completely. The mixture was then allowed to cool to 20° C. with stirring, in the course of which precipitate formation set in at 42° C. The precipitated crystals were filtered off with suction and washed with isopropanol (200 ml). After drying under air, 822 g (47.5% based on the racemate used; 95% based on the (R)-3-amino-1-butanol present in the racemate) of (S)-mandelic salt of (R)-3-amino-1-butanol were obtained with an optical purity of 88.4% ee in the bound amine.

The resulting (S)-mandelic salt of (R)-3-amino-1-butanol was suspended in isopropanol (3 l) and the mixture was heated to boiling. The resulting clear solution was cooled to 20° C. with stirring. The salt which precipitated out was filtered off with suction, washed with isopropanol (100 ml) and dried under air. This gave 590 g of (S)-mandelic salt of (R)-3-amino-1-butanol with an optical purity of 98.5% ee in the bound amine.

The (S)-mandelic salt of (R)-3-amino-1-butanol obtained from this recrystallization was suspended in isopropanol (2.4 l) and water (35 ml), and the mixture was heated to boiling. The resulting clear solution was cooled to 20° C. with stirring. The salt which precipitated out was filtered off with suction, washed with isopropanol (100 ml) and dried in a vacuum drying cabinet. This gave 556 g (overall yield: 32.2% based on the racemate used) of (S)-mandelic salt of (R)-3-amino-1-butanol with an optical purity of 99.6% ee in the bound amine.

$^1$H NMR (400 MHz, $D_2O$) δ=1.30 (d, J=7 Hz, 3H); 1.75 (mc, 1H); 1.90 (mc, 1H); 3.45 (mc, 1H); 1.65-1.80 (m, 2H); 5.00 (s, 1H); 7.35-7.50 (m, 5H).

Melting point: 133-135° C.

Optical rotation: $[\alpha]_D$=77.4° (c=3.0 in $H_2O$)

1.2 Release of (R)-3-amino-1-butanol From the (S)-mandelic Salt Thereof

The (S)-mandelic salt of (R)-3-amino-1-butanol obtained in Example 1.1 (372 g, 1.54 mol) was suspended in triethanolamine (1 l) at 80° C., and the slurry was admixed with sodium methoxide (277.6 g, 1.54 mol; 30% in methanol), which gave a clear solution. This was heated to 100° C. and vacuum was applied. In a stepwise manner, a pressure of 750, 500, 250, 100, 50 and finally 20 mbar was applied. Through an attached Claisen distillation head (no return stream, no column), a clear distillate distilled over at a top temperature of 50 to 60° C., which was predominantly methanol. The pressure was then lowered further to 5 mbar, and (R)-3-amino-1-butanol distilled over at a top temperature of 76° C. The product was distilled once again in a water jet pump vacuum, in the course of which (R)-3-amino-1-butanol distilled over at 93° C. and 26 mbar. This gave 125 g (91% of theory) of (R)-3-amino-1-butanol as a colorless liquid with an optical purity of 99.6% ee.

The optical purity of (R)-3-amino-1-butanol was determined by means of GC. To this end, (R)-3-amino-1-butanol (200 mg) and triethylamine (300 mg) were dissolved in diethyl ether (15 ml) and admixed with trifluoroacetic anhydride (0.6 ml). After stirring for 30 minutes, saturated ammonium chloride solution (5 ml) was added and the mixture was stirred for a further 15 minutes. Subsequently, the mixture was left to stand until two phases had formed, and a sample of the upper clear phase was analyzed by GC.

Column: Hydrodex-TBDAc, 25 m×0.25 mm, Macherey & Nagel
Inlet temperature: 250° C.
Detector temperature: 250° C.
Injection volume : 0.5 μl
Mode: Split
Split ratio: 100:1
Carrier gas: He
Flow: 0.8 ml/min (constant flow)
Program:
Initial temperature: 135° C.
Initial time: 10 min
Rate: 5° C./min
Final temperature: 170° C.
Final time: 35 min
Retention times:
R enantiomer: 17.68 min (N-trifluoroacylated) 21.23 min (N,O-bis-trifluoroacylated)
S enantiomer: 18.24 min (N-trifluoroacylated) 20.11 min (N,O-bis-trifluoroacylated)

2. Enantiomer Separation of 1-benzyloxy-3-butylamine
2.1 Preparation of the (S)-mandelic Salt of (R)-1-benzyloxy-3-butylamine (S)-Mandelic acid (8.5 g, 56 mmol) and acetic acid (3.4 g, 56 mmol) were initially charged in 65 ml of isopropanol at room temperature and admixed while stirring with racemic 1-benzyloxy-3-butylamine (20 g, 112 mmol). In the course of this, a temperature increase to about 40° C. occurred. The reaction mixture was heated to boiling until the precipitated salts had dissolved completely. Then the mixture was left to cool to room temperature overnight. The precipitated crystals were filtered off with suction and washed with cold isopropanol (20 ml). After drying under reduced pressure, 6.4 g (17.3% based on the racemate used; 34.6% based on the (R)-1-benzyloxy-3-butylamine present in the racemate) of (S)-mandelic salt of (R)-1-benzyloxy-3-butylamine were obtained with an optical purity of 48.4% ee in the bound amine.

The resulting (S)-mandelic salt of (R)-1-benzyloxy-3-butylamine was recrystallized three times in isopropanol (30, 20 and 15 ml). This gave 1.8 g of (S)-mandelic salt of (R)-1-benzyloxy-3-butylamine with an optical purity of 99% ee in the bound amine.

$^1$ H NMR (400 MHz, $D_2O$) δ=1.25 (d, J=7 Hz, 3H); 1.75 (mc, 1H); 1.90 (mc, 1H); 3.45 (mc, 1H); 3.70 (m, 2H); 4.55 and 4.60 (AB system, $J_{AB}$=12 Hz, 2H); 5.00 (s, 1H); 7.35-7.50 (m, 10H).

Melting point: 128-130° C.

2.2 Release of (R)-1-benzyloxy-3-butylamine From the (S)-mandelic Salt Thereof

The (S)-mandelic salt of (R)-1-benzyloxy-3-butylamine obtained in Example 2.1 was introduced into water (10 ml) and admixed with 50% NaOH until the pH was 13. The mixture was extracted with diethyl ether (2 x 50 ml), the organic phase was dried over sodium sulfate and the solvent was removed in an oil pump vacuum. This gave 0.8 g (9% based on the racemate used in Example 2.1) of (R)-1-benzyloxy-3-butylamine as a colorless oil with an optical purity of 99% ee.

3. Enantiomer Separation of 1-tert-butoxy-3-butylamine 3.1 Preparation of the (R)-mandelic Salt of (R)-1-Cert-butoxy-3-butylamine (R)-Mandelic acid (15.2 g, 0.1 mol) and acetic acid (6.0 g, 0.1 mol) were initially charged in 150 ml of isopropanol at room temperature and admixed while stirring with racemic 1-tert-butoxy-3-butylamine (29 g, 0.2 mol). In the course of this, a temperature increase to about 50° C. occurred. The reaction mixture was heated to boiling until the precipitated salts had dissolved completely. Then the mixture was allowed to cool to room temperature overnight. The precipitated crystals were filtered off with suction and washed with cold isopropanol (20 ml). After drying under reduced pressure, 20 g (33.7% based on the racemate used; 67.3% based on the (R)-1-tert-butoxy-3-butylamine present in the racemate) of (R)-mandelic salt of (R)-1-tert-butoxy-3-butylamine were obtained with an optical purity of 70% ee in the bound amine.

The resulting (R)-mandelic salt of (R)-1-tert-butoxy-3-butylamine was recrystallized twice in isopropanol (100 ml each time). This gave 12 g of (R)-mandelic salt of (R)-1-tert-butoxy-3-butylamine with an optical purity of 99.2% ee in the bound amine.

$^1$H NMR (400 MHz, D$_2$O)δ=1.25 (s, 9H); 1.35 (d, J=7 Hz, 3H); 1.75 (mc, 1H); 1.90 (mc, 1H); 3.50 (sext, J=7 Hz, 1H); 3.65 (mc, 2H); 5.00 (s, 1H); 7.35-7.50 (m, 5H).

Melting point: 178° C.

3.2 Release of (R)-1-tert-butoxy-3-butylamine From the (R)-mandelic Salt Thereof The (R)-mandelic salt of (R)-1-tert-butoxy-3-butylamine obtained in Example 3.1 was introduced into water (50 ml) and admixed with 50% NaOH until the pH was 13. The mixture was extracted with diethyl ether (2 x 50 ml), the organic phase was dried over sodium sulfate and the solvent was removed in a water jet pump vacuum. This gave 5.5 g (19% based on the racemate used in Example 3.1) of (R)-1-tert-butoxy-3-butylamine as a colorless oil with an optical purity of 99.2% ee.

The invention claimed is:

1. A process for separating an enantiomer mixture of (R)- and (S)-3-amino-1-butanol optionally protected on the oxygen atom, comprising the following steps:
  (i) reacting an enantiomer mixture of the compounds of the formulae I-R and I-S

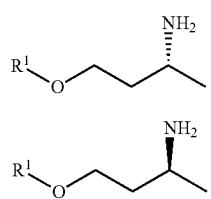

wherein R$^1$ is hydrogen or a protecting group selected from C$_1$-C$_4$-alkyl with (S)- or (R)-mandelic acid and an acid different from this (S)- or (R)-mandelic acid used
  (ii) removing and isolating the (S)- or (R)-mandelic salt of the compound of the formula I-R formed in step (i);
  (iii) optionally purifying the (S)- or (R)-mandelic salt of the compound of the formula I-R isolated in step (ii);
  (iv) releasing the compound of the formula I-R from the (S)- or (R)-mandelic salt thereof and if desired deprotecting the compound of the formula I-R in which R$^1$ is not hydrogen to obtain (R)-3-amino-1-butanol; and
  (v) optionally releasing the enriched compound of the formula I-S and optionally deprotecting the compound of the formula I-S wherein R$_1$ is not hydrogen to obtain enriched (S)-3-amino-1-butanol;
wherein the compound of the formula I-R is released from the (S)- or (R)-mandelic salt thereof in step (iv) by reacting the (S)- or (R)-mandelic salt of the compound of the formula I-R obtained in step (ii) or (iii) with a base selected from alkali metal C$_1$-C$_4$-alkoxides in a solvent which possesses a boiling point at least 10° C. higher than 3-amino-1-butanol and is selected from organic amines having a melting point of at most 50° C. and a boiling point of at least 180° C.

2. A process for preparing essentially enantiomerically pure (R)-3-amino-1-butanol which optionally bears a protecting group on the oxygen atom, comprising the following steps:
  (i) reacting an enantiomer mixture of the compounds of the formulae I-R and I-S

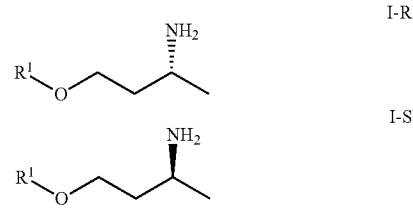

wherein R$^1$ is hydrogen or a protecting group selected from C$_1$-C$_4$-alkyl with (S)- or (R)-mandelic acid and an acid different from this (S)- or (R)-mandelic acid used;
  (ii) removing and isolating the (S)- or (R)-mandelic salt of the compound of the formula I-R formed in step (i);
  (iii) optionally purifying the (S)- or (R)-mandelic salt of the compound of the formula I-R isolated in step (ii); and
  (iv) releasing the compound of the formula I-R from the (S)- or (R)-mandelic salt thereof and optionally deprotecting the compound of the formula I-R wherein R$^1$ is not hydrogen to obtain (R)-3-amino-1-butanol;
wherein the compound of the formula I-R is released from the (S)- or (R)-mandelic salt thereof in step (iv) by reacting the (S)- or (R)-mandelic salt of the compound of the formula I-R obtained in step (ii) or (iii) with a base selected from alkali metal C$_1$-C$_4$-alkoxides in a solvent which possesses a boiling point at least 10° C. higher than 3-amino-1-butanol and is selected from organic amines having a melting point of at most 50° C. and a boiling point of at least 180° C.

3. The process of claim 1, wherein R$^1$ is hydrogen.

4. The process of claim 1, wherein (S)-mandelic acid is used in step (i), the (S)-mandelic salt of the compound I-R is removed and isolated in step (ii), the (S)-mandelic salt of the compound I-R is optionally purified in step (iii), and the compound I-R is released from the (S)-mandelic salt thereof in step (iv).

5. The process of claim 1, wherein (S)- or (R)-mandelic acid is used in step (i) in an amount of 0.8 to 1.2 mol, based on 1 mol of the compound of the formula I-R present in the enantiomer mixture.

6. The process of claim 5, wherein (S)- or (R)-mandelic acid is used in an approximately equimolar amount, based on the amount of compound of the formula I-R present in the enantiomer mixture.

7. The process of claim 1, wherein the acid different from the (S)-or (R)-mandelic acid used is used in step (i) in an amount of 0.8 to 1.2 mol, based on 1 mol of the compound of the formula I-S present in the enantiomer mixture.

8. The process of claim 7, wherein the acid different from the (S)-or (R)-mandelic acid used is used in an approximately equimolar amount, based on the amount of compound of the formula I-S present in the enantiomer mixture.

9. The process of claim 1, wherein the acid different from (S)- or (R)-mandelic acid is achiral.

10. The process of claim 9, wherein the acid different from (S)- or (R)-mandelic acid is acetic acid.

11. The process of claim 1, wherein step (i) is performed in the presence of at least one $C_1$-$C_4$-alcohol which optionally comprises water in an amount of 0.1 to 10% by weight, based on the total weight of the at least one $C_1$-$C_4$-alcohol and water, as a solvent.

12. The process of claim 11, wherein step (i), in the case that $R^1$ is hydrogen, is performed in isopropanol which comprises 0.1 to 10% by weight of water, based on the total weight of isopropanol and water, as a solvent.

13. The process of claim 1, wherein the (S)- or (R)-mandelic salt of the compound of the formula I-R is removed and isolated by precipitation of the (S)- or (R)-mandelic salt of the compound of the formula I-R and isolation of the precipitate.

14. The process of claim 1, wherein the (S)- or (R)-mandelic salt of the compound of the formula I-R isolated in step (ii) is subsequently purified further once or more than once by recrystallization in step (iii).

15. The process according to claim 1, wherein the organic amines are selected from diethanolamine and triethanolamine.

* * * * *